United States Patent
Zhang et al.

(10) Patent No.: US 10,570,176 B2
(45) Date of Patent: Feb. 25, 2020

(54) ANTI-HEPATITIS B VIRUS X PROTEIN POLYPEPTIDE PHARMACEUTICAL

(71) Applicant: TIANJIN TOPTECH BIO-SCIENCE & TECHNOLOGY CO., LTD., Tianjin (CN)

(72) Inventors: Xiaodong Zhang, Tianjin (CN); Lihong Ye, Tianjin (CN)

(73) Assignee: Tianjin TOPTECH Bio-Science & Technology Co., Ltd., Tianjin (CN)

( * ) Notice: Subject to any disclaimer, the term of this patent is extended or adjusted under 35 U.S.C. 154(b) by 0 days.

(21) Appl. No.: 15/557,209

(22) PCT Filed: Oct. 16, 2015

(86) PCT No.: PCT/CN2015/092132
§ 371 (c)(1),
(2) Date: Oct. 23, 2017

(87) PCT Pub. No.: WO2016/145840
PCT Pub. Date: Sep. 22, 2016

(65) Prior Publication Data
US 2018/0334478 A1 Nov. 22, 2018

(30) Foreign Application Priority Data
Mar. 13, 2015 (CN) .......................... 2015 1 0111013

(51) Int. Cl.
*A61K 38/10* (2006.01)
*C07K 7/08* (2006.01)
*A61P 31/20* (2006.01)
*A61K 39/29* (2006.01)

(52) U.S. Cl.
CPC .............. *C07K 7/08* (2013.01); *A61K 38/10* (2013.01); *A61K 39/292* (2013.01); *A61P 31/20* (2018.01)

(58) Field of Classification Search
CPC .................. A61K 38/10; C07K 7/08
See application file for complete search history.

(56) References Cited

U.S. PATENT DOCUMENTS

| | | | | |
|---|---|---|---|---|
| 5,141,851 A | * | 8/1992 | Brown ................. | C07K 1/1077 435/15 |
| 5,358,934 A | * | 10/1994 | Borovsky .............. | A01N 43/36 435/226 |
| 5,464,821 A | * | 11/1995 | Stig ........................ | C07C 237/12 514/20.8 |

FOREIGN PATENT DOCUMENTS

| | | | | |
|---|---|---|---|---|
| CN | 102675422 A | * | 9/2012 | .............. C07K 7/08 |
| CN | 103992388 A | | 8/2014 | |
| EP | 2687537 A1 | * | 1/2014 | .............. C07K 7/08 |
| JP | 8500829 A | | 1/1996 | |
| JP | 9509182 A | | 9/1997 | |
| WO | 94/05311 | | 3/1994 | |
| WO | 95/23166 | | 8/1995 | |

OTHER PUBLICATIONS

Feifel et al. D-Peptide Ligands for the Co-chaperone DnaJ. The Journal Of Biological Chemistry. May 15, 1998, vol. 273, No. 20, pp. 11999-12002. (Year: 1998).*
L. Brinckerhoff et al. "Terminal Modifications Inhibit Proteolytic Degradation of an Immunogenic MART-1(27-35) Peptide: Implications for Peptide Vaccines" Int. J. Cancer: 83, 326-334 (1999).
A. Chevigne et al. "Engineering and screening the N-terminus of chemokines for drug discovery" Biochemical Pharmacology 82: 1438-1456 (2011).
D. Bang et al. "Total Chemical Synthesis and X-ray Crystal Structure of a Protein Diastereomer: [D-Gln35]Ubiquitin" Angew. Chem. Int. Ed. 44:3852-3856 (2005).
J. Mitchell et al. "D-Amino Acid Residues in Peptides and Proteins" Proteins: Structure, Function, and Genetics 50:563-571(2003).

* cited by examiner

*Primary Examiner* — Jeffrey E. Russel
(74) *Attorney, Agent, or Firm* — Milstein Zhang & Wu LLC; Duan Wu, Esq.; Yin "Philip" Zhang, Esq.

(57) ABSTRACT

The present invention relates to the field of polypeptide medicine, and relates to polypeptides against hepatitis B virus X Protein and uses thereof. Specifically, the present invention relates to polypeptides comprising D-amino acids, which have a function of inhibiting hepatitis B virus X protein, and inhibit HBx activities, inhibit replication of hepatitis B virus DNA and expression of related antigens (e.g., HBeAg) at molecular level, cellular level and animal level, and further inhibit hepatitis and hepatic cirrhosis caused by hepatitis B virus infection and liver cancer that occurs on the basis of hepatic cirrhosis. The polypeptides can be widely used in the prevention and treatment of liver diseases after hepatitis B infection, including hepatitis, hepatic cirrhosis, and liver cancer.

8 Claims, 6 Drawing Sheets

Specification includes a Sequence Listing.

```
                            SEQUENCE LISTING

<160> NUMBER OF SEQ ID NOS: 12

<210> SEQ ID NO 1
<211> LENGTH: 12
<212> TYPE: PRT
<213> ORGANISM: Artificial
<220> FEATURE:
<223> OTHER INFORMATION: Synthesized polypeptide with modified peptides
      of D-amino acids
<220> FEATURE:
<221> NAME/KEY: PEPTIDE
<222> LOCATION: (2)..(2)
<223> OTHER INFORMATION: Xaa is D-Serine
<220> FEATURE:
<221> NAME/KEY: PEPTIDE
<222> LOCATION: (3)..(3)
<223> OTHER INFORMATION: Xaa is D-Alanine
<220> FEATURE:
<221> NAME/KEY: PEPTIDE
<222> LOCATION: (4)..(4)
<223> OTHER INFORMATION: Xaa is D-Valine
<220> FEATURE:
<221> NAME/KEY: PEPTIDE
<222> LOCATION: (5)..(5)
<223> OTHER INFORMATION: Xaa is D-Methionine
<220> FEATURE:
<221> NAME/KEY: PEPTIDE
<222> LOCATION: (6)..(6)
<223> OTHER INFORMATION: Xaa is D-Phenylalanine
<220> FEATURE:
<221> NAME/KEY: PEPTIDE
<222> LOCATION: (7)..(8)
<223> OTHER INFORMATION: Xaa is D-Serine
<220> FEATURE:
<221> NAME/KEY: PEPTIDE
<222> LOCATION: (9)..(9)
<223> OTHER INFORMATION: Xaa is D-Lysine
<220> FEATURE:
<221> NAME/KEY: PEPTIDE
<222> LOCATION: (10)..(10)
<223> OTHER INFORMATION: Xaa is D-Glutamic Acid
<220> FEATURE:
<221> NAME/KEY: PEPTIDE
<222> LOCATION: (11)..(11)
<223> OTHER INFORMATION: Xaa is D-Arginine

<400> SEQUENCE: 1

Gly Xaa Xaa Xaa Xaa Xaa Xaa Xaa Xaa Xaa Xaa Gly
1               5                   10

<210> SEQ ID NO 2
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: PEPTIDE
```

```
<222> LOCATION: (2)..(2)
<223> OTHER INFORMATION: Xaa is D-Serine

<400> SEQUENCE: 2

Gly Xaa Ala Val Met Phe Ser Ser Lys Glu Arg Gly
1               5                   10

<210> SEQ ID NO 3
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: PEPTIDE
<222> LOCATION: (3)..(3)
<223> OTHER INFORMATION: Xaa is D-Alanine

<400> SEQUENCE: 3

Gly Ser Xaa Val Met Phe Ser Ser Lys Glu Arg Gly
1               5                   10

<210> SEQ ID NO 4
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: PEPTIDE
<222> LOCATION: (4)..(4)
<223> OTHER INFORMATION: Xaa is D-Valine

<400> SEQUENCE: 4

Gly Ser Ala Xaa Met Phe Ser Ser Lys Glu Arg Gly
1               5                   10

<210> SEQ ID NO 5
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: PEPTIDE
<222> LOCATION: (5)..(5)
<223> OTHER INFORMATION: Xaa is D-Methionine

<400> SEQUENCE: 5

Gly Ser Ala Val Xaa Phe Ser Ser Lys Glu Arg Gly
1               5                   10

<210> SEQ ID NO 6
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: PEPTIDE
<222> LOCATION: (6)..(6)
<223> OTHER INFORMATION: Xaa is D-Phenylalanine

<400> SEQUENCE: 6

Gly Ser Ala Val Met Xaa Ser Ser Lys Glu Arg Gly
1               5                   10

<210> SEQ ID NO 7
<211> LENGTH: 12
```

```
<212> TYPE: PRT
<213> ORGANISM: Artificial
<220> FEATURE:
<223> OTHER INFORMATION: Synthesized
<220> FEATURE:
<221> NAME/KEY: PEPTIDE
<222> LOCATION: (7)..(7)
<223> OTHER INFORMATION: Xaa is D-Serine

<400> SEQUENCE: 7

Gly Ser Ala Val Met Phe Xaa Ser Lys Glu Arg Gly
1               5                   10

<210> SEQ ID NO 8
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: PEPTIDE
<222> LOCATION: (8)..(8)
<223> OTHER INFORMATION: Xaa is D-Serine

<400> SEQUENCE: 8

Gly Ser Ala Val Met Phe Ser Xaa Lys Glu Arg Gly
1               5                   10

<210> SEQ ID NO 9
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: PEPTIDE
<222> LOCATION: (9)..(9)
<223> OTHER INFORMATION: Xaa is D-Lysine

<400> SEQUENCE: 9

Gly Ser Ala Val Met Phe Ser Ser Xaa Glu Arg Gly
1               5                   10

<210> SEQ ID NO 10
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: PEPTIDE
<222> LOCATION: (10)..(10)
<223> OTHER INFORMATION: Xaa is D-Glutamic Acid

<400> SEQUENCE: 10

Gly Ser Ala Val Met Phe Ser Ser Lys Xaa Arg Gly
1               5                   10

<210> SEQ ID NO 11
<211> LENGTH: 12
<212> TYPE: PRT
<213> ORGANISM: Artificial
<220> FEATURE:
<223> OTHER INFORMATION: Synthesized
<220> FEATURE:
<221> NAME/KEY: PEPTIDE
<222> LOCATION: (11)..(11)
<223> OTHER INFORMATION: Xaa is D-Arginine

<400> SEQUENCE: 11
```

```
Gly Ser Ala Val Met Phe Ser Ser Lys Glu Xaa Gly
1               5                   10
```

<210> SEQ ID NO 12
<211> LENGTH: 12
<212> TYPE: PRT
<213> ORGANISM: Artificial
<220> FEATURE:
<223> OTHER INFORMATION: Synthesized polypeptide

<400> SEQUENCE: 12

```
Gly Ser Ala Val Met Phe Ser Ser Lys Glu Arg Gly
1               5                   10
```

ANTI-HEPATITIS B VIRUS X PROTEIN POLYPEPTIDE PHARMACEUTICAL

CROSS-REFERENCE TO RELATED APPLICATIONS

This application is the U.S. national phase of and claims priority to PCT/CN2015/092132, filed Oct. 16, 2015, which claims the benefit of priority from Chinese Application No. 201510111013.0, filed on Mar. 13, 2015.

REFERENCE TO SEQUENCE LISTING

Sequence listings and related materials in the ASCII text file named "FNS004-Listing-2_ST25.txt" and created on Jun. 9, 2019 with a size of about 4 kilobytes, is hereby incorporated by reference.

TECHNICAL FIELD

The present invention relates to the field of polypeptide medicine, and specifically, relates to polypeptides against hepatitis B virus X Protein comprising D-amino acids and uses thereof.

BACKGROUND

Liver cancer is one of the malignant tumors that can lead to death. Its malignant degree is high, in China, the mortality rate of liver cancer is the second highest, only less than the mortality rate of gastric cancer. According to statistics, there are about 300,000 people with newly developed liver cancer each year in China, and about 110,000 people die each year because of this disease. Hepatitis B Virus (HBV) infection may lead to hepatitis, hepatic cirrhosis and primary liver cancer. In China, more than 80% of liver cancer patient had their liver cancer developed after HBV infection, which is also referred to as post-hepatitis B liver cancer.

The HBV is a DNA virus having a length of about 3.2 Kb, and contains overlapping open reading frames (ORFs) that are responsible for transcription and expression of the hepatitis B virus surface antigen (HBsAg), the hepatitis B virus core antigen (HBcAg), the hepatitis B virus polymerase, and the hepatitis B virus X antigen (HBxAg) (also known as hepatitis B virus X protein, HBx), wherein HBx is an indispensable factor in HBV DNA replication. Because HBx is an indispensable factor in HBV DNA replication, to inhibit the function of HBx may lead to suppression of HBV infection, as well as the subsequent hepatitis and hepatic cirrhosis.

In addition, as a trans-activator factor, HBx can promote the growth and proliferation of liver cancer, thus is also known as oncoprotein. Studies at molecular level, cellular level and animal level have shown that HBx has strong effect in promoting proliferation and migration of liver cancer cells. Transgenic mouse experiments also showed that HBx can cause liver cancers. The results of numerous studies further indicated that persistence of HBV infection could lead to chronic liver diseases, including chronic hepatitis, repeated chronic hepatitis, which subsequently causes hyperplasia of fibrous connective tissue in liver tissues and hepatic cirrhosis, and most of liver cancer based on hepatic cirrhosis. It has been well established that HBx plays a critical role in the development and progress of chronic liver diseases (including hepatitis, hepatic cirrhosis and liver cancer). Consequently, HBx becomes an important target for preventing and treating liver diseases.

Currently, the treatment of liver cancer is mainly through surgery, supplemented with interventional therapies, whereas chemotherapy is usually not very effective. Clinical data show that the rate of finding HBsAg and HBxAg positively expressed in liver cancer tissues is more than 80% or even 90%. Since HBx is an important pathogenic factor in the occurrence and development of liver cancer, identifying its specific inhibitors would have great theoretical and clinical significance. However, due to incompleteness of three-dimensional conformation analysis of HBx, it is rather difficult to design its chemical inhibitors through HBx's three-dimensional conformation information.

Fragmental polypeptides can be used as medicine, and they have already been widely used in clinical practices. For example, thymopeptide is a thymopentin extracted from calf thymus with the function of promoting lymphocyte transformation, enhancing phagocytic activity of macrophages, and can be used to treat a variety of immunodeficiency diseases. The characteristics of the polypeptide drugs include well-defined pharmacokinetics effects, safety, and easy to be manufactured. However, because polypeptide drugs tend to be affected by protease in vivo and have low stability and short half-life, the efficacy thereof is usually not ideal.

Amino acids can exist in the configuration of levorotation (L-amino acids) and dextrorotation (D-amino acids). All natural amino acids in human or animal body are L-type without any D-amino acids. Proteolytic enzymes for D-amino acids do not exist in organisms. Therefore, if the L-type natural amino acids are substituted with corresponding D-types without affecting the amino acid sequence when preparing polypeptide drugs, stability of the polypeptide drugs in blood can also be improved. However, how to improve degradation resistance of polypeptide drugs while not reducing its binding characteristics so as to maintain the pharmaceutical efficacy remains an important issue in polypeptide drug development.

The inventors of the present invention have discovered a polypeptide with a function of inhibiting hepatitis B virus X protein and solely comprised of natural L-amino acids (please refer to Chinese invention patent no. ZL201110061840.5 for details, the disclosure thereof is hereby incorporated by reference in its entirety). The polypeptide comprises the amino acid sequence as shown in SEQ ID NO:12. The polypeptide has a function of inhibiting HBx activities at molecular level, cellular level and animal level and can be used in the treatment or prevention of hepatitis, hepatic cirrhosis and liver cancer caused by hepatitis B virus infection.

SUMMARY OF INVENTION

The present invention relates to polypeptides against hepatitis B virus X Protein and uses thereof. Said polypeptides are polypeptides comprising D-amino acids, which have a function of inhibiting hepatitis B virus X protein, and inhibit HBx activities, inhibit DNA replication of hepatitis B virus and expression of related antigens (e.g., HBeAg) at molecular level, cellular level and animal level, and further inhibit hepatitis and hepatic cirrhosis caused by hepatitis B virus infection and liver cancer that occurs on the basis of hepatic cirrhosis.

In one aspect, the present invention provides an isolated polypeptide, which comprises the amino acid sequence as shown in SEQ ID NO: 1, or functional fragments thereof, or functional variants of the amino acid sequence or functional fragments thereof, and one or more L-amino acids in the amino acid sequences of said amino acid sequence, said functional fragments or said functional variants is substituted by D-amino acid; said polypeptide has a function of inhibiting hepatitis B virus X protein, and capable of inhibiting the occurrence and development of chronic liver diseases resulted from hepatitis B virus infection.

Preferably, the polypeptide of the present invention comprises an amino acid sequence that has at least 70% (preferable at least 80%, 85%, 90%, 95%, 99% or higher) identity with the amino acid sequence as shown in SEQ ID NO: 1.

In specific embodiments of the present invention, the amino acid sequence of the polypeptide is any one of the amino acid sequences as shown in SEQ ID NOS:2-11.

In present invention, the chronic liver diseases resulted from hepatitis B virus infection comprise hepatitis, hepatic cirrhosis, and liver cancer.

In another aspect, the present invention provides use of the polypeptide in the manufacture of medicaments for treating and preventing chronic liver diseases resulted from hepatitis B virus infection. Specifically, the medicament can be a therapeutic vaccine against hepatitis B virus. The medicament can be a pharmaceutical composition comprising any one of the polypeptides of the present invention, which may contain optional pharmaceutical carrier.

As compared to the polypeptides having identical amino acid sequences but solely comprised of L-amino acids, the polypeptides of the present invention not only exhibit good stability, but also exert surprisingly remarkable pharmaceutical effects, especially in the function of inhibiting DNA replication of hepatitis B virus and expression of related antigens (e.g., HBeAg). Accordingly, the polypeptides can be widely used in the prevention and treatment of chronic liver diseases resulted from hepatitis B virus infection, including hepatitis, hepatic cirrhosis, and liver cancer.

DETAILED DESCRIPTION

Figure 1:
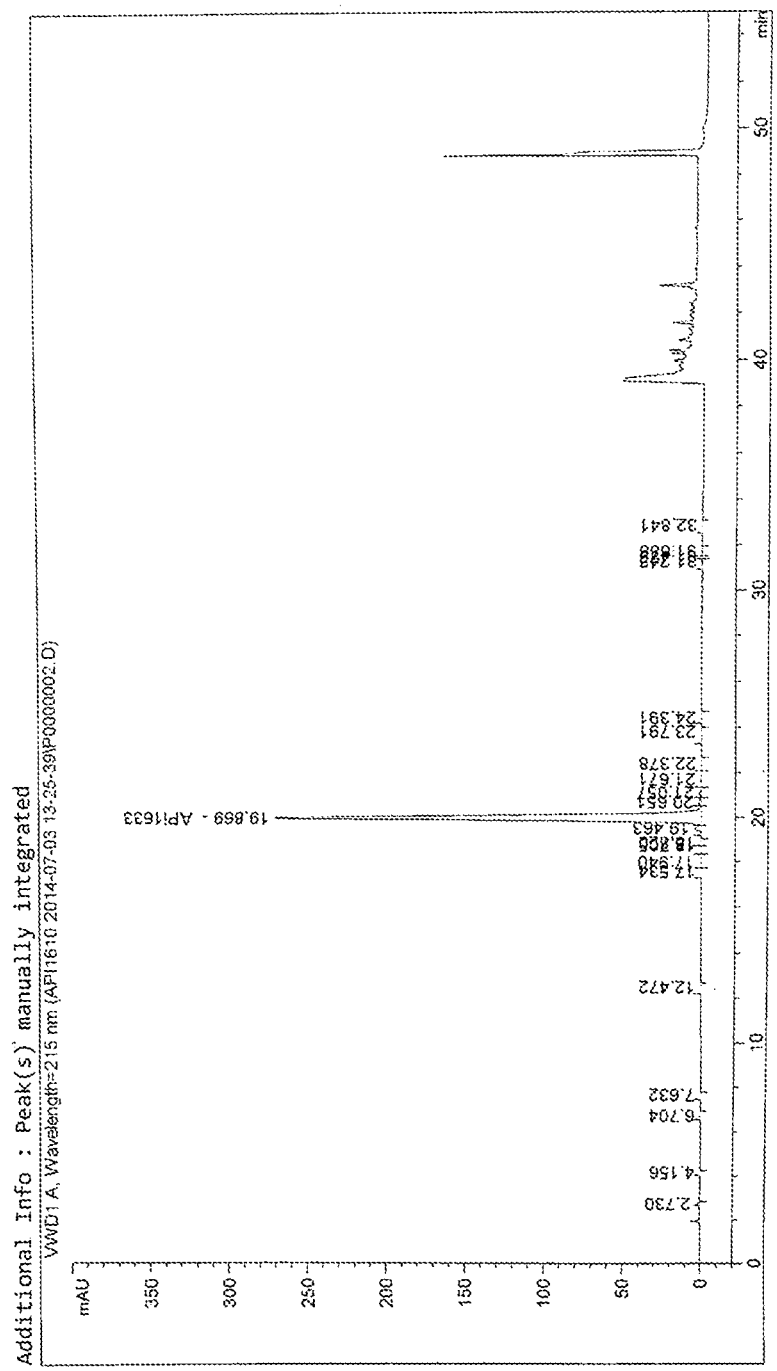
FIG. 1. HPLC analysis result of purified artificially synthesized polypeptide D-TTK001.

In the present invention, including the description and claims, unless otherwise specified, the following terms are used with the following meanings:

In the invention, abbreviations are used to describe amino acids, including L-amino acids and D-amino acids. The abbreviations are listed in Table 1.

TABLE 1A

Abbreviation Listing

| Amino acids | Three-letter symbols of L-amino acids | One-letter symbols of L-amino acids | Three-letter symbols of D-amino acids | One-letter symbols of L-amino acids |
|---|---|---|---|---|
| Alanine | Ala | A | D-Ala | D/A |
| Arginine | Arg | R | D-Arg | D/R |
| Asparagine | Asn | N | D-Asn | D/N |
| Aspartic acid | Asp | D | D-Asp | D/D |
| Cysteine | Cys | C | D-cys | D/C |
| Glutamine | Gln | Q | D-Gln | D/Q |
| Glutamic acid | Glu | E | D-Glu | D/E |
| Glycine | Gly | G | D-Gly | D/G |
| Histidine | His | H | D-His | D/H |
| Isoleucine | Ile | I | D-Ile | D/I |
| Leucine | Leu | L | D-Leu | D/L |
| Lysine | Lys | K | D-Lys | D/K |
| Methionine | Met | M | D-Met | D/M |
| Phenylalanine | Phe | F | D-Phe | D/F |
| Proline | Pro | P | D-Pro | D/P |
| Serine | Ser | S | D-Ser | D/S |
| Threonine | Thr | T | D-Thr | D/T |
| Tryptophan | Trp | W | D-Trp | D/W |
| Tyrosine | Tyr | Y | D-Tyr | D/Y |
| Valine | Val | V | D-Val | D/V |

In the invention, in amino acid sequence of polypeptides, symbol "D-*" is used to indicate any D-amino acid substituting the original L-amino acid in the specific position of the polypeptide.

As a reference, amino acids can exist in the configuration of levorotation (L-amino acids) and dextrorotation (D-amino acids). L-amino acids are the amino acids naturally existing in nature and most biological systems. In addition, naturally existing polypeptides are comprised of L-amino acids, thus can be referred to as L-polypeptides. D-amino acids are "mirror images" of the corresponding L-amino acids. Although D-polypeptides (polypeptides completely comprised of D-amino acids) do not exist naturally, these polypeptides can be artificially synthesized to form three-dimensional protein structures.

"Isolated" refers to separating a substance from its original environment (e.g., its natural environment if it is naturally generated). For example, a naturally generated polypeptide existing in a live animal means it has not been isolated, whereas the same polypeptide separated partially or completely from the substances with which polypeptide usually coexist in natural systems means isolated. Such polypeptide may exist as a part of a vector, or a part of a composition; since the vector and the composition are not a component of its natural environment, they are still isolated.

The term "purified" as used herein means an increased status in purity, wherein "purity" is a relative term, and should not be narrowly construed as absolute purity. For example, the purity can be at least about 50%, or greater than 60%, 70%, 80%, or 90%, or even reach to 100%.

As used in the present invention, isolated substance is separated from its original environment. The polypeptides naturally existed within living cells are not isolated; however, the same polypeptides that are separated from the substances that polypeptides coexist with in the natural state should be regarded as isolated, and while the purity is improved, thus is purified.

The so-called "amino acid sequence" or "polypeptide" refers to a peptide, oligopeptide, polypeptide or protein and their partial fragment, which consists of amino acids that are connected with each other by peptide bonds. When amino acid sequence in the present invention is related to the amino acid sequence of a naturally occurred protein molecule or a described known artificially synthesized polypeptide, such naturally occurred protein molecule or known polypeptide is not meant to limit the amino acid sequence for the entire natural amino acid sequence of said protein molecule or said known polypeptide. Amino acid sequence of the invention can comprise additional peptides, such as multiple histidine tag (His-tag), or epitope tag like Myc, FLAG, or the like. Amino acid sequence of the invention can also comprise artificially synthesized D-amino acids, which substitute one or more L-amino acids in the amino acid sequence of said protein molecule or said known polypeptide.

The "functional fragment" of a polypeptide as used herein refers to any part or portion of the polypeptide of the invention, which retains substantially similar or identical biological activity or function of the original polypeptide of which it is a part (the parent polypeptide).

The "functional variant" of a polypeptide as used herein refers to amino acid sequences having substantially similar or identical biological activity or function of the polypeptide or amino acid sequence, including, for example, 1) the original amino acid sequence with one or more amino acid deletion and/or one or more amino acid addition; or 2) one or more of amino acid in the original amino acid sequence substituted by one or more conservative or non-conservative amino acid; or 3) a group in one or more amino acid of the amino acid sequence substituted by other group; or 4) the original amino acid sequence fused with another molecule or compound (such as sugar, lipids, polyethylene glycol, etc.); or 5) original amino acid sequence fused with additional polypeptide sequence (e.g., a leader sequence or a secretion signal sequence or a polypeptide sequence used for purifying purpose); or 6) a retroinverso analogs of the original amino acid sequence; or 7) combination of the above.

Wherein, "deletion" refers to the deletion of one or a plurality of amino acids from the amino acid sequence.

"Insert" or "add" refers to the increasing of one or a plurality of amino acids caused by the change of amino acid sequence compared with the molecules of the natural presence or before the change.

"Substitution" refers to one or a plurality of amino acids substituted by different amino acids.

"Deletion, substitution or addition of one or a plurality of amino acids" refers to the use of known methods of mutating nucleic acid such as directed mutagenesis method to delete, substitute or add a number of amino acids at the degree that deletion, substitution or addition is possible. Above mutation is not limited to artificially induced mutations by known methods, but also includes a naturally occurring mutation in nucleic acid or protein which can be separated and purified.

The percentage of "homology" or "identity" of amino acid sequence refers to a percentage of sequence identity or similarity in the comparison with two or more amino acid sequences. There are many methods to determine the percentage of sequence identity for those skilled in the art, such as the MEGALIGN program (Lasergene Software Packages, DNASTA Inc., Madison, Wis.). MEGALIGN program can compare two or more sequences based on the different types of method such as Cluster Method (see Higgins & Sharp, *Gene* 73:237-244 (1988)). Each set of sequence is aligned by clusters by checking the distance between the pairs, and then the cluster is assigned by pairs or groups. The percentage of similarity of two amino acid sequences, Sequence A and Sequence B, can be calculated by the following formula:

[(the number of matching residues between Sequence A and Sequence B)/(the number of residues of sequence A–the number of residues of the sequence A in the intervals–the number of residues of sequence B in the intervals)]×100%

In the invention, "chronic liver diseases resulted from hepatitis B virus infection" refers to liver diseases caused by hepatitis B virus infection, including chronic hepatitis, hepatic cirrhosis after hyperplasia of fiberous connective tissue in liver tissue caused by repeated hepatitis, and liver cancers based on hepatic cirrhosis.

In the invention, "treatment" and "prevention" and words derived therefrom, do not mean 100% or completely treatment or prevention, but can be identified as the treatment or prevention extent approved by those skilled in the art. In the invention, "prevention" could be understood as delaying the onset of the disease, or its symptoms or disorders.

Polypeptide

The present invention provides isolated or purified polypeptides. Said polypeptides are polypeptides having the amino acid sequence Gly-Ser-Ala-Val-Met-Phe-Ser-Ser-Lys-Glu-Arg-Gly (i.e., SEQ ID NO:12, herein referred to as L-TTK001) wherein one or more natural L-amino acids are substituted with corresponding artificially synthesized D-amino acids. The present invention demonstrated that such polypeptides can significantly inhibit activity of HBx, thus exhibit function of inhibiting DNA replication of hepatitis B virus and expression of related antigens (e.g., HBeAg), and further inhibit the occurrence and development of chronic liver diseases after hepatitis B virus infection, especially hepatitis, hepatic cirrhosis and liver cancer.

In the invention, any number of L-amino acids in L-TTK001 polypeptide can be substituted with corresponding D-amino acids, such as 1, 2, 3, 4, 5, 6, 7, 8, 9, or 10 L-amino acids can be substituted.

According to one embodiment of the invention, amino acid sequence of the polypeptide of the invention is the sequence of L-TTK001 wherein 10 L-amino acids except glycine are substituted with corresponding D-amino acids (i.e., Gly-D-Ser-D-Ala-D-Val-D-Met-D-Phe-D-Ser-D-Ser-D-Lys-D-Glu-D-Arg-Gly, SEQ ID NO:1, herein referred to as D-TTK001).

Since natural peptidase cannot use D-amino acids as substrates, by using corresponding D-amino acids to substitute one or more L-amino acids of the polypeptide, it is possible to obtain polypeptides with higher in vivo stability. Studies have shown that, for example, presence of D-amino acids at N-terminal or C-terminal may increase in vivo stability of the polypeptides (Powell et al., *Pharm. Res.* 10: 1268-1273 (1993)). But since D-amino acids and L-amino acids have different chirality, i.e., different stereochemical configuration, "mirror image" structures are formed, polypeptides comprising D-amino acids not always have same binding ability or biological function as the original L-polypeptides. Therefore, it is hard to predict whether two polypeptide molecules having same amino acid sequences but having different amino acid configurations have same functions. Accordingly, except conducting actual experiments on the modified polypeptides comprising D-amino acids, one cannot determine whether the polypeptides comprising D-amino acids have same efficacies as the original polypeptides. Practically, if it is necessary to modify a pharmaceutical polypeptide comprising L-amino acids into a pharmaceutical polypeptide comprising D-amino acids, in order to maintain or enhance its pharmacodynamic function, it is required for the technical personnel to conduct numerous experiments and continually optimization on how to specifically modify the polypeptide, such as which one or more amino acids to be substituted or which position to be substituted.

In general, for a polypeptide containing D-amino acid residues, the less the number of L-amino acid residues substituted by D-amino acid residues, the less the change in binding ability of the polypeptide. When a large number of L-amino acids are substituted, changes in polypeptide binding ability and biological efficacy will be increased accordingly, even resulted in its total loss.

However, inventors of the present invention discovered through experimentation that when one or more L-amino acids of polypeptide L-TTK001 are substituted by D-amino acids, said substituted polypeptide maintains a substantially same biological function as L-TTK001 polypeptide, including: inhibiting replication and expression of hepatitis B virus at cellular level and animal level, treating viral hepatitis caused by hepatitis virus at animal level, and inhibiting growth of liver cancer cells afterward.

Inventors of the present invention also surprisingly discovered that even when all L-amino acids of L-TKK001 were substituted with artificially synthesized D-amino acids (that is, the obtained polypeptide is D-TTK001), in vitro binding of said substituted polypeptide to HBx protein has not been significantly changed. For example, according to in vitro binding analysis results, in vitro binding of L-polypeptide L-TTK001 to HBx (8 nM) showed no significant difference as compared to in vitro binding of D-TTK001 to HBx (35 nM).

Since amino acids contained in D-TTK001 are all D-amino acids, D-TTK001 polypeptide also has good pharmacokinetic performances. Therefore, the inventors discovered that, polypeptides of the present invention, e.g., D-TTK001, can achieve effective pharmaceutical efficacy with much lower doses than L-TTK001 and with administration methods different to that of L-TTK001, such as by animal tail intravenous injection.

Relevantly, the inventors discovered that the polypeptides of the invention exhibit more remarkable effects than L-polypeptides (e.g., L-TTK001) on inhibiting DNA replication of HBV and expression of related antigens (e.g., HBeAg), and further inhibiting the occurrence and development of chronic liver diseases after hepatitis B virus infection (including hepatitis, hepatic cirrhosis and liver cancer) especially for hepatitis, because of the pharmacokinetic property and stability of the polypeptides. For example, effective dose of D-polypeptide on the inhibition of HBeAg secretion level is orders of magnitude lower than that of L-polypeptide; whereas based on the improvement in stability, polypeptides of the invention are also more advantageous than L-polypeptides that are comprised of L-amino acids on the selection of administration routes.

The present invention also provides various functional fragments of polypeptides of the invention. Said functional fragments can be any fragments of the continuous amino acid sequence of the polypeptide of the present invention on condition that the functional fragments can retain the biological activity of the parent polypeptide by a similar extent, by the same extent, or by a higher extent as compared to the parent polypeptide, e.g., inhibition of HBx activity. With reference to the parent polypeptide, the functional fragments can have, e.g., approximately 10%, 20%, 30%, 40%, 50%, 60%, 70%, 80%, 90%, 95%, 100%, 105%, 110%, 120%, 150%, 200% or even greater activity of that provided by the parent polypeptide. Said functional fragments can also contain additional amino acids at either or both of the amino terminus and carboxyl terminus of various fragments of the continuous amino acid sequence, for example, amino acids different from that in the amino acid sequence of the parent polypeptide. Preferably, said additional amino acids do not hinder the biological function of said functional fragment, e.g., inhibition of HBx activity, inhibition of replication and expression of HBV virus, and effectively inhibition of the occurrence and development of hepatitis and development of liver cancer. More desirably, said additional amino acids can lead to enhanced biological activity when compared with the biological activity of the parent polypeptide. Preferably, the amino acid sequences of the functional fragments of the peptides of the present invention have at least 70% sequence identity with the amino acid sequences of the polypeptides of the present invention; more preferable, the amino acid sequences of the functional fragments of the peptides of the present invention have at least 75%, or 80%, or 85%, or 90%, or 95% sequence identity with the amino acid sequences of the polypeptides of the present invention.

In addition, the functional variants of the polypeptide and the functional fragments thereof in the present invention are also included within the scope of the invention. The functional variants of the polypeptide of the invention and functional fragments thereof should retain substantial similar or identical biological activity with the parent polypeptide or the functional fragments thereof, e.g., inhibition of the HBx activity, inhibition of replication and expression of HBV virus, treatment of viral hepatitis caused by HBV virus at animal level of HBV transgenic mice, and inhibition of malignant phenotype of liver cancer cells. With reference to the polypeptide of the invention or the functional fragments thereof, the functional fragments can have, e.g., approximately 50%, 60%, 70%, 80%, 90%, 95% or 100% sequence identity with the amino acid sequences of the parent polypeptides or the functional fragments thereof. Preferably, the amino acid sequences of the functional fragments have at least 70% sequence identity with the amino acid sequences of the polypeptides of the invention or functional fragments thereof more preferably, the functional variant of the polypeptide of the invention and functional fragments thereof differ from the parent polypeptide or functional fragment thereof by only 1-3 amino acids; most preferably, the functional variant of the polypeptide of the present invention and functional fragments thereof differ from the parent polypeptide or functional fragment thereof by only 1 amino acid.

For example, the present invention includes amino acid sequences of the polypeptides of the invention or functional fragments thereof subjected to at least one conservative amino acid substitutions. Specifically, the polypeptides of the invention or functional fragments thereof can be subjected to 1, 2, 3, 4, 5, or more conservative amino acid substitutions, which also belong to the scope of the present invention. Alternatively, the present invention also includes amino acid sequences of the polypeptides of the invention or functional fragments thereof subjected to at least one non-conservative amino acid substitutions from the parent polypeptide or functional fragments thereof. Specifically, the amino acid sequence having 2, 3, 4, 5, or more non-conservative amino acid substitutions from the parent polypeptide or functional fragments thereof is included. In these cases, it is preferable for the amino acid substitutions to not interfere with or inhibit the biological activities of the polypeptides of the invention or functional fragments thereof. More preferable, the amino acid substitutions further increase the biological activities of the polypeptides of the invention or functional fragments thereof.

Conservative amino acids substitutions are well-known in the art, which means amino acid substitutions in which one amino acid having certain physical and/or chemical properties is substituted with another amino acid that has the same chemical or physical properties. Skilled in the art understand that conservative amino acid substitutions may not cause significant changes in the structure or function of the protein. For instance, typical conservative amino acid substitutions include an acidic amino acid substituted with another acidic amino acid (e.g., Asp or Glu), an amino acid with a nonpolar side chain substituted with another amino acid with a nonpolar side chain (e.g., Ala, Gly, Val, Ile, Leu, Met, Phe, Pro, Trp, or Val, etc.), a basic amino acid substituted with another basic amino acid (Lys, Arg, etc.), an amino acid with a polar side chain substituted with another amino acid with a polar side chain (Asn, Cys, Gln, Ser, Thr, or Tyr, etc.), an aromatic amino acid (Trp, Phe, or Tyr, etc.) substituted with another aromatic amino acid, etc.

Polypeptides of the invention (including functional fragments thereof) and functional variants thereof can be of any length, i.e., can comprise any number of amino acids, provided that the polypeptide (or functional fragments thereof) and functional variants thereof retain essential biological activities of the parent polypeptide, e.g., inhibition of HBx activity, inhibition of replication and expression of HBV virus at cellular level and animal level, and treatment of viral hepatitis caused by HBV virus including inhibiting growth of liver cancer cells of later stages. For example, polypeptides of the invention (including functional fragments and functional variants) can be 4 to 2000 amino acids long, such as 5, 6, 7, 8, 9, 10, 11, 12, 13, 14, 15, 16, 18, 20, 25, 30, 40, 50, 60, 70, 80, 90, 100, 125, 150, 175, 200, 300, 400, 500, 700, 800, 1000 or more amino acids in length. Preferably, the polypeptides of the invention are 6 to 20 amino acids in length, and meet the requirements on pharmacokinetics and half-life of polypeptide drugs.

In one embodiment, the polypeptides of the invention and functional variants of the functional fragments thereof have only one amino acid different from the parent polypeptide of SEQ ID NO: 1, and have similar biological activity and function as the parent polypeptide of SEQ ID NO: 1, for example, inhibition of HBx activity, and effectively inhibition of cancer cells, preferably liver cancer cells, especially liver cancer cells that express HBx.

The polypeptides of the invention (including functional fragments) and functional variants thereof described herein may also comprise a cell-penetrating peptide (CPP). Such CPP facilitates the entry of polypeptide of the invention across the cell membrane and into the cell. CPPs are known in the art. See, for example, Deshayes et al., *Cell. Mol. Life Sci.* 62: 1839-1849 (2005); El-Andaloussi et al., *Curr. Pharm. Design.* 11: 3597-3611(2005). The CPP described herein can be any of those known in the art.

The polypeptides of the invention (including functional fragments) and functional variants thereof, for example, can be lipidated (e.g., fatty acidated), glycosylated, amidated, carboxylated, phosphorylated, esterified, N-acylated, cyclized via a disulfide bond, converted into an acid addition salt, dimerized or polymerized, and/or conjugated.

The polypeptides of the invention (including functional fragments) and functional variants thereof, including derivatives thereof such as fatty acid derivatives, can be a monomer peptide, a dimer peptide or a multimer peptide.

The polypeptides of the invention (including functional fragments) and functional variants thereof can be obtained by methods known in the art (see, for instance, Chan et al., *Fmoc Solid Phase Peptide Synthesis*, Oxford University Press, Oxford, United Kingdom, 2005; Reid, R., *Peptide and Protein Drug Analysis*, Marcel Dekker Company, 2000; and U.S. Pat. No. 5,449,752). In addition, polypeptides can be recombinantly produced using standard recombinant methods (see, for instance, Sambrook et al., *Molecular Cloning: A Laboratory Manual* 3rd ed., Cold Spring Harbor Press, Cold Spring Harbor, N.Y. 2001). Further, some of the polypeptides of the invention (including functional fragments and functional variants thereof) can be isolated and/or purified from a source, such as a plant, a bacterium, an insect, a mammal, e.g., a rat, a human, etc. Methods of isolation and purification are well-known in the art. Alternatively, the polypeptides described herein (including functional fragments and functional variants thereof) can be synthesized or obtained from commercial companies.

Conjugate

The present invention also includes conjugates, e.g., bioconjugates, comprising the polypeptides of the present invention (including functional fragments or functional variants) or peptidomimetics. Conjugates, as well as methods of synthesizing conjugates in general, are known in the art (see, for instance, Hudecz, F., *Methods Mol Biol.* 298: 209-223 (2005) and Kirin et al., *Inorg Chem.* 44(15): 5405-5415 (2005)).

Pharmaceutical Composition

Above-mentioned materials of the present invention, including polypeptides (including functional fragments) and functional variants thereof and conjugates, etc., (hereinafter collectively referred to as "the materials of the invention") can be isolated, purified, synthesized and/or recombined.

The materials of the invention can also be formulated into a composition, such as a pharmaceutical composition. In this regard, the invention provides a pharmaceutical composition comprising any of the polypeptides (including functional fragments and functional variants) and peptidomimetics, and a pharmaceutically acceptable carrier. The pharmaceutical composition of the invention containing any of the materials of the invention can comprise more than one material of the invention, e.g., two or more different polypeptides. Alternatively, the pharmaceutical composition can comprise a material in combination with another active pharmaceutical agent or drug. Preferably, said another active pharmaceutical agent or drug can include, such as a chemotherapeutic agent, e.g., asparaginase, busulfan, carboplatin, cisplatin, damiorabicin, doxorubicin, fluorouracil, gemcitabine, hydroxyurea, methotrexate, paclitaxel, rituximab, vinblastine, vincristine, etc.

In a preferred embodiment of the invention, the pharmaceutical composition comprises the material of the invention in combination with a lipid. Said lipid can be any lipid, including a fatty acid, a phospholipid, a sterol, a sphingolipid, a terpene, a glycerolipid, a glycerophospholipid, a prenol lipid, a saccharolipid, a polyketide, and the like. Such lipids are known in the art.

With respect to pharmaceutical compositions, the pharmaceutically acceptable carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to the skilled in the art and are readily available to the public. Preferably, the pharmaceutically acceptable carrier is chemically inert to the active agent(s) and has no detrimental side effects or toxicity under the conditions of use.

The choice of carrier will be determined in part by the particular material of the invention, as well as by the particular method used to administer the material of the invention. Accordingly, there are a variety of suitable formulations of the pharmaceutical composition of the invention. The following formulations for oral, aerosol, parenteral, subcutaneous, intravenous, intramuscular, intraarterial, intrathecal, intraperitoneal, rectal, and vaginal administration are exemplary and are in no way of limiting. More than one route can be used to administer the materials of the invention, and in certain situations, a particular route can provide a more immediate and more effective response than another route.

In a preferred embodiment of the invention, the pharmaceutical composition is a topical formulation, an intravenous formulation, or a subcutaneous formulation. In a preferred embodiment of the invention, the pharmaceutical composition is a topical formulation. Topical formulations are well-known to the skilled in the art. Such formulations are particularly suitable in the context where the invention is for application to the skin. The topical formulation of the invention can be, for instance, a cream, a lotion, an ointment, a patch, an oil, a paste, a spray, e.g., an aerosol spray, a gel, a roll-on liquid, a solid stick, etc. Preferably, the topical formulation of the invention is a cream, a lotion, an ointment, or a patch.

Formulations suitable for oral administration can be comprised of (a) liquid solutions, such as an effective amount of the material of the invention dissolved in diluents, such as water, saline, or orange juice; (b) capsules, tablets, and lozenges, each containing a predetermined amount of the active ingredient, as solids or granules; (c) powders; (d) suspensions in an appropriate liquid; and (e) suitable emulsions. Liquid formulations can include diluents, such as water and alcohols, for example, ethanol, benzyl alcohol, and polyethylene glycols, either with or without the addition of a pharmaceutically acceptable surfactant. Capsule forms can be of the ordinary hard- or soft-shelled gelatin type, containing, for example, surfactants, lubricants, and inert fillers, such as lactose, sucrose, calcium phosphate, and corn_starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the material of the invention in a flavoring agent, usually sucrose or acacia, as well as pastilles comprising the material of the invention in an inert matrix, such as gelatin and glycerin, or sucrose and acacia, in addition, emulsions, gels, and the like containing excipients known in the art.

The materials of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as non-pressured preparations, such as in a nebulizer or an atomizer. Such spray formulations also may be used to spray mucosa.

Formulations suitable for parenteral administration include aqueous and non-aqueous isotonic sterile injection solutions, which can contain anti-oxidants, buffers, bacteriostats, and solutes that render the formulation isotonic with the blood of the intended recipient, and aqueous and non-aqueous sterile suspensions, which can include suspending agents, solubilizers, thickening agents, stabilizers, and preservatives. The material of the invention can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, oils, fatty acids, fatty acid esters or glycerides, or acetylated fatty acid glycerides with or without the addition of a pharmaceutically acceptable surfactant, such as a soap or a detergent, suspending agent, such as pectin, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut oil, soybean oil, sesame oil, cottonseed oil, olive oil, petroleum oil, and mineral oil. Suitable fatty acids for use in parenteral formulations include oleic acid, stearic acid, and isostearic acid.

Suitable soaps for use in parenteral formulations include fatty acid alkali metal salts, and triethanolamine salts, and contain suitable detergents include (a) cationic detergents such as, dimethyl dialkyl ammonium halides, and alkyl pyridinium halides, (b) anionic detergents such as, alkyl, aryl, and olefin sulfonates, alkyl, olefin, ether, and monoglyceride sulfates, and sulfosuccinates, etc., (c) nonionic detergents such as, fatty amine oxides, fatty acid alkanolamides, and polyoxyethylenepolypropylene copolymers, etc., (d) amphoteric detergents such as, alkyl-β-aminopropionates, and 2-alkyl-imidazoline quaternary ammonium salts, and (e) mixtures thereof.

The parenteral formulations will typically contain from about 0.5% to about 25% (weight in volume percentage) of the material of the invention in solution. Preservatives and buffers may be used. In order to minimize or eliminate irritation at the site of injection, such compositions may contain one or more nonionic surfactants having a hydrophile-lipophile balance (HLB). The quantity of surfactant in such formulations will typically range from about 5% to about 15% (weight in volume percentage). Suitable surfactants include polyethylene glycol sorbitan fatty acid esters and high molecular weight adducts of ethylene oxide with a hydrophobic base, formed by the condensation of propylene oxide with propylene glycol. The parenteral formulations can be presented in single-dose or multi-dose sealed containers, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The materials of the invention or compositions comprising the material of the invention can be made into injectable formulations. The requirements for effective pharmaceutical carriers for injectable compositions are well-known to those of ordinary skill in the art. Preferably, when administering to cells, e.g., dendritic cells, the cells are administered via injection.

Additionally, the materials of the invention, or compositions comprising such materials, can be made into suppositories by mixing with a variety of bases, such as emulsifying bases or water-soluble bases. Formulations suitable for vaginal administration can be presented as pessaries, tampons, creams, gels, pastes, foams, or spray formulations containing, in addition to the active ingredient, such carriers as are known in the art to be appropriate.

It will be appreciated by the skilled in the art that, in addition to the above-described pharmaceutical compositions, the materials of the invention can be formulated as inclusion complexes, such as cyclodextrin inclusion complexes, or liposomes.

For purposes of the invention, the amount or dose of the material of the invention administered should be sufficient to effect, e.g., a therapeutic or prophylactic response, in the subject or animal over a reasonable time frame. For example, the dose of the material of the invention should be sufficient to inhibit proliferation of a diseased cell, or treat or prevent a disease (e.g., tumor or cancer) in a period of from about 2 hours or longer, e.g., 12 to 24 or more hours, from the time of administration. In certain embodiments, the time period could be even longer. The dose will be determined by the efficacy of the particular material of the invention and the condition of the animal (e.g., human), as well as the body weight of the animal (e.g., human) to be treated. Many assays for determining an administered dose are known in the art. The dose of the material of the invention also will be determined by the existence, nature and extent of any adverse side effects that might accompany the administration of a particular material.

One of ordinary skill in the art will readily appreciate that the materials of the invention can be modified in any number of ways, such that the therapeutic or prophylactic efficacy of the materials is increased through the modification. For instance, the materials can be conjugated either directly or indirectly through a linker to a targeting moiety. The practice of conjugating compounds, e.g., the materials of the invention, to targeting moieties is known in the art. See, for instance, Wadwa et al., *J. Drug Targeting* 3: 111 (1995) and U.S. Pat. No. 5,087,616. In a further embodiment, the materials of the invention can be modified into a depot form, such that the manner in which the materials is released into the body to which it is administered is controlled with respect to time and location within the body (see, for example, U.S. Pat. No. 4,450,150). Depot forms of the materials of the invention can be, for example, an implantable composition comprising the materials of the invention and a porous or non-porous material, such as a polymer, wherein the materials of the invention are encapsulated by or diffused throughout the material and/or degradation of the non-porous material. The depot is then implanted into the desired location within the body and the materials of the invention are released from the implant at a predetermined rate.

The pharmaceutical compositions of the invention, including polypeptides (including functional fragments) and functional variants thereof, can be used in methods of preventing and inhibiting hepatitis B virus infection-induced chronic liver diseases, including viral hepatitis and the resulted hepatic cirrhosis and liver cancers. Ordinary skill in the art should be readily understood that the chronic liver diseases induced by hepatitis B virus described in the present invention may be present in any host. Preferably, the host is a mammal. Specially preferably, the host is a human.

The present invention will be further illustrated below with reference to the specific examples. It should be understood that these examples are only used to describe the invention but not to limit the scope of the invention. The experimental methods with no specific conditions described in the following examples are generally performed under conventional conditions, and the materials used without specific description are purchased from common chemical reagents corporation.

EXAMPLES

Example 1: Design and Preparation of Polypeptides

Artificial Synthesis of the Fragment of Polypeptide D-TTK001:

Polypeptides having the amino acid sequence Gly-D-Ser-D-Ala-D-Val-D-Met-D-Phe-D-Ser-D-Ser-D-Lys-D-Glu-D-Arg-Gly (SEQ ID NO: 1) (hereinafter referred to as D-TTK001) are synthesized by artificial synthetic methods. The polypeptide was prepared through solid phase peptide synthesis method, such as was carried out on the AAPPTEC Apex396 Peptide Synthesizer (purchased from Hong Kong Universal Analytical & Testing Instruments Ltd.); the synthesis was performed in accordance with the sequence of SEQ ID NO: 1, from C-terminus carboxyl terminal to N-terminus amino terminal, to synthesize the amino acid in the sealed explosion-proof glass reactor. This refers to that the first amino acid monomer added into the amino acid sequence of Gly-D-Ser-D-Ala-D-Val-D-Met-D-Phe-D-Ser-D-Ser-D-Lys-D-Glu-D-Arg-Gly was Gly in the C-terminus, followed by D-Arg, and then D-Glu, until the last D-Ser and Gly in the N-terminus were added. The resulting peptide was obtained by repeating adding, reacting and synthesizing. The solid phase peptide synthesis greatly reduced the difficulties in purification of the resulting peptides in each of the steps. Side chains of the amino acids involved in the reaction were protected in order to prevent side-reactions. Terminal carboxyl groups were unbounded thus must be activated before reaction.

The artificially synthesized polypeptide D-TTK001 was analyzed by HPLC (with PLC Agela C18 column). FIG. 1 showed that the purity is 97.2%.

Example 2

A. Measurement of In Vitro Binding Ability

Figure 2:
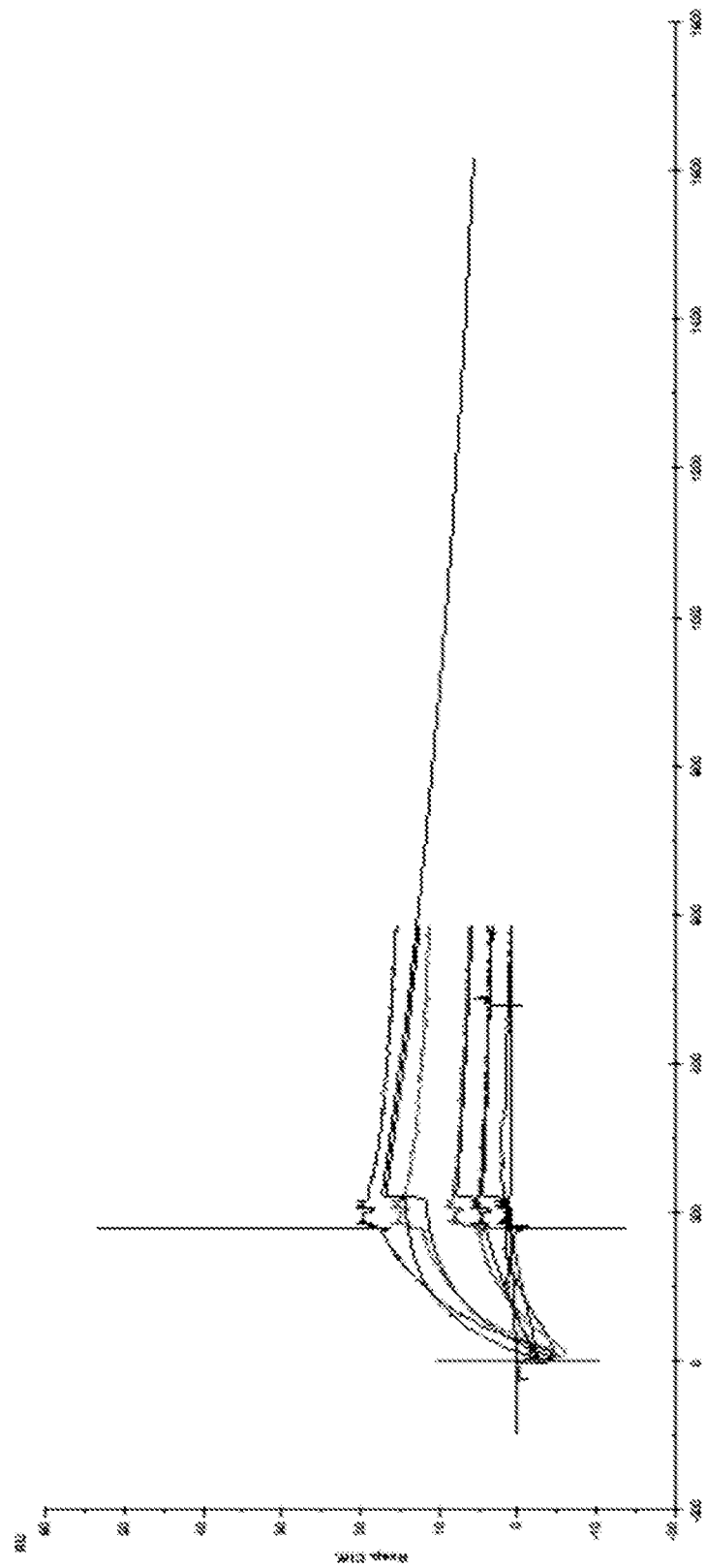
FIG. 2. Experimental results of in vitro binding of polypeptides of the invention to target protein HBx using Biacore 3000.

The recombinant plasmid (pET-30a-HBx) expressing HBx gene was self-constructed and preserved (Zhang H, et al. *J Biomed Biotechnol*, doi:10.1155/2009/289068), and then expression and purification of HBx were conducted according to above reference for the measurement of in vitro binding ability. Biacore 3000 biomolecular interaction analyzing unit (manufactured by GE Healthcare) was utilized to measure in vitro binding ability of polypeptide D-TTK001 to recombinantly expressed HBx protein. Polypeptide at different concentrations were injected for 180 seconds at a rate of 30 µL/min. In dissociation stage, HBS-EP buffer was injected for 900 seconds at a rate of 30 µL/min, then at a rate of 30 µL/min, 2 shots of 1 mM NaOH were injected for 20 seconds to regenerate the chip. All signals were calibrated using channel 1 as the reference channel. Binding measurement was conducted twice, respectively, wherein in the first measurement, HBX was injected into the channel of the coupled polypeptide and the blank channel at concentrations of 0 nM, 10 nM, 50 nM, 100 nM, 500 nM and 600 nM, respectively. Binding time was 180 seconds and dissociation time was 400 seconds. On chip surface, 1 mM NaOH was injected for 20 seconds at a rate of 30 µL/min for regeneration. Results were kinetically analyzed by software, as shown in FIG. 2. In the second measurement, HBX was injected into the channel of coupled polypeptide and the blank channel at concentrations of 0 nM, 10 nM, 50 nM, 588 nM, 1 µM, and 2 µM, respectively. Binding time was 180 seconds and dissociation time was 400 seconds. On chip surface, 1 mM NaOH was injected for 20 seconds at a rate of 30 µL/min for regeneration. Results were kinetically analyzed by BIA Evaluation Software.

Results of two binding measurements are listed in Table 1B.

TABLE 1B

Analysis results of binding affinity

| Sample | ka (1/Ms) | kd (1/s) | KD (M) |
|---|---|---|---|
| D-TTK001~HBx First measurement | 2.72e4 | 8.11e−4 | 2.99e−8 |
| D-TTK001~HBx Second measurement | 6.76e4 | 2.72e−3 | 4.03e−8 |

The data shows that although in vitro binding of D-TTK001 to HBx was lower than that of L-polypeptide anti-HBxP1#, there is no difference in the order of magnitude.

B. In Vitro Efficacy Experiments

1. Cell Lines:

TABLE 2A

Cell lines utilized in the experiments

| Cell line | Characteristics, use and notes | Origin |
|---|---|---|
| HepG2-X | HepG2 stably transfected with HBx gene Wang Q, et al. *Neoplasia*. 2010; 12(2): 103-15. | self-constructed and preserved |
| HepG2.2.15 | HepG2 stably transfected with whole-genome of HBV | Purchased from Shanghai Jinma Biotech Co., Ltd. |
| HepAD38 | Liver cancer cell stably integrated with HBV DNA, its expression regulated by tetracycline | Purchased from Shanghai Sixin Biotech Co., Ltd. |

2. Major Reagents:

| Reagent | Origin |
|---|---|
| RPMI1640 medium | Gibco |
| DMEM medium | Gibco |
| Lipofectamine 2000 | Invitrogen |
| Myllicin | Solarbio |
| Trypsin | BBI |
| Fetal bovine serum | Hyclone |
| HBeAg assay kit | Shanghai Kehua Bio-engineering Co., Ltd |

3. Analysis of function of D-TTK001 on HBeAg secreation in liver cancer cells utilizing enzyme-linked immunosorbent assay (ELISA)

(1) Cell Culture (i) Biosafety cabinet was ultraviolet sterilized for 30 min and purged for 30 min; DMEM/F12 (1:1) culture medium containing 15% fetal bovine serum, HepAD38 cells (or HepG2.2.15 cells) were taken out, sterilized with 75% alcohol, and placed in the biosafety cabinet.

(ii) Under aseptic conditions, discard old culture medium, add 3 mL 1×PBS each time, wash twice, add 1 mL 0.25% trypsin, the cells were digested until cell rounding as observed in microscope. Add 5 mL culture medium, dispense cells, count with hemocytometer, and dilute with culture medium to a cell number of $1~2\times10^4$ cells/mL.

(iii) Plating 96-well plate. Under aseptic conditions, discard old culture medium, add 3 mL 1×PBS each time, wash twice, add 1 mL 0.05% trypsin, the cells were digested until cell rounding as observed in microscope. Add 10 mL culture medium, dispense cells, count with hemocytometer, and dilute with DMEM/F12(1:1) culture medium, add 100 µL cell suspension into each well to a cell number of $1\sim2\times10^3$ cells/mL. The outer-most wells are not added with cells. Culturing until cell attachment (usually 12 hrs.) and extension. Subsequent tests can be conducted when cells are in good condition.

(2) Applying D-TTK001 (or L-TTK001, i.e., anti-HBxP1#) to liver cancer HepAD38 cells (or HepG2.2.15 cells)

10 mM D-TTK001 (or L-TTK001) mother solution was serially diluted from high concentration to low concentration, added into liver cancer HepAD38 cells (or HepG2.2.15 cells) culture solution to obtain final concentrations of D-TTK001 (or L-TTK001) of 0.1 µM, 1 µM, 10 and 100 µM in respective groups. For negative control group, add 10 µL of sterilized ddH$_2$O, and incubate for 72 hrs. in a 37° C., 5% CO$_2$ incubator.

(3) Applying ELISA to measure HBeAg content in HepAD38 cell (or HepG2.2.15 cell) culture medium (i) Balancing: place HBeAg assay kit in room temperature for 30 min.

(ii) Preparing solution: dilute concentrated wash liquid for 25 times with purified water.

(iii) Taking out the plate: take out the reaction plate according to experimental requirements (3 wells for negative control, 1 well for positive control, and 1 well for blank control).

(iv) Adding sample: add 75 µL of test samples or negative/positive control into respective wells, gently shake and mix.

(v) Incubating: after sealed with microplate sealer, incubate at 37° C. for 60 min.

(vi) Adding enzyme: add 50 µL of enzyme conjugates into each well except for blank wells, gently shake and mix.

(vii) Incubating: after sealed with microplate sealer, incubate at 37° C. for 30 min.

(viii) Washing plate: remove microplate sealer carefully, manually wash plate for 5 times, pat dry.

(ix) Developing color: add 50 µL each of color-developing agent A and B liquid, gently shake and mix, develop color in dark placed at 37° C. for 30 min.

(x) Stopping: add 50 µL of stop solution into each well, gently shake and mix, measure the result in ten minutes. Set wavelength of microplate reader to 450 nm, measure OD value for each well after zero setting with blank wells.

Figure 3:
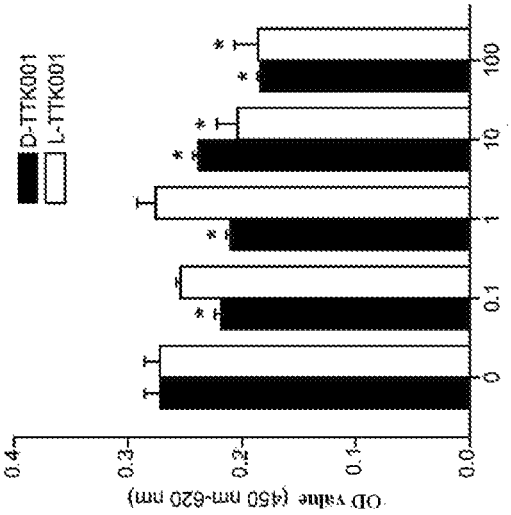
FIG. 3. Analysis of the effects of polypeptides of the invention on HBeAg secretion levels of liver cancer HepAD38 cells integrated with HVB DNA at cellular level. Results showed that HBeAg secretion levels of liver cancer HepAD38 cells integrated with HVB DNA were inhibited after 48 hours treatment with 0.1, 1, 10, and 100 μM of artificially synthesized polypeptide D-TTK001 or L-TTK001 (i.e., anti-HBxP1#) with a dose dependency. Minimum effective dose of D-TTK001 is 0.1 μM; minimum effective dose of L-TTK001 is 10 μM. Therefore, the effect of D-TTK001 on HBeAg is better than that of L-TTK001 on HBeAg. Student's t-test is employed for statistical analysis, * $P<0.05$, ** $P<0.01$.
Figure 4:
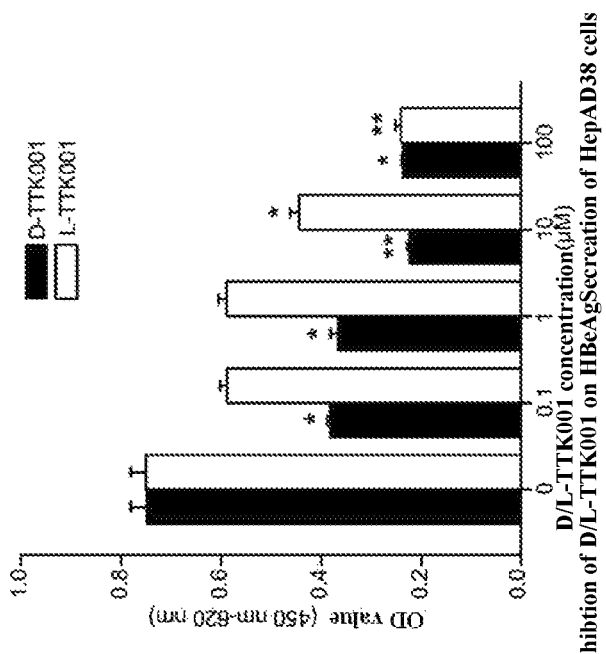
FIG. 4. Analysis of the effects of polypeptides of the invention on HBeAg secretion levels of HepG2.2.15 cells at cellular level. Results showed that HBeAg secretion levels of HepG2.2.15 cells were inhibited after 48 hours treatment with 0.1, 1, 10, and 100 μM of artificially synthesized polypeptide D-TTK001 or L-TTK001 (i.e., anti-HBxP1#) with a dose dependency. Minimum effective dose of D-TTK001 is 0.1 μM; minimum effective dose of L-TTK001 is 10 μM. Therefore, the effect of D-TTK001 on HBeAg is better than that of L-TTK001 on HBeAg. Student's t-test is employed for statistical analysis, * $P<0.05$, ** $P<0.01$.

As shown in FIG. 3 and FIG. 4, D-TTK001 (or L-TTK001) exhibited inhibition effect on HBeAg secretion levels of HepAD38 cells (or HepG2.2.15 cells) with a dose dependency. Minimum effective dose of D-TTK001 is 0.1 µM; minimum effective dose of L-TTK001 is 10 µM. Therefore, the effect of D-TTK001 on HBeAg is better than that of L-TTK001 on HBeAg. Student's t-test is employed for statistical analysis, * $P<0.05$, ** $P<0.01$.

4. MTT Assay (1) Plating cells: suspend HepAD38 cells at exponential phase in RPMI1640 medium with 10% FBS, and plate 4000-5000 cells in a 96-well plate with 100 µL per well.

(2) Culturing cells: within 12 hrs. for adhesion of cultured cells, add different concentrations of synthesized D-TTK001 (or L-TTK001) polypeptides from Example 1 (0.1 µM, 1 µM, 10 µM and 100 µM) into 8 wells for each concentration, and incubate for 48 hrs. in common condition.

(3) Coloration: add 20 µL of MTT solution (5 mg/mL MTT in PBS buffer (pH7.4)) for each well.

(4) Incubate for 4 hrs., and carefully aspirate off the supernatant from the wells. Add 150 µL of DMSO into each well, shake for 10 min until the crystals were dissolved.

(5) Comparison: Read in an ELISA reader at 490 nm to measure the absorbance for each well. Results were calculated using Student's t-test.

Figures 5, 6:
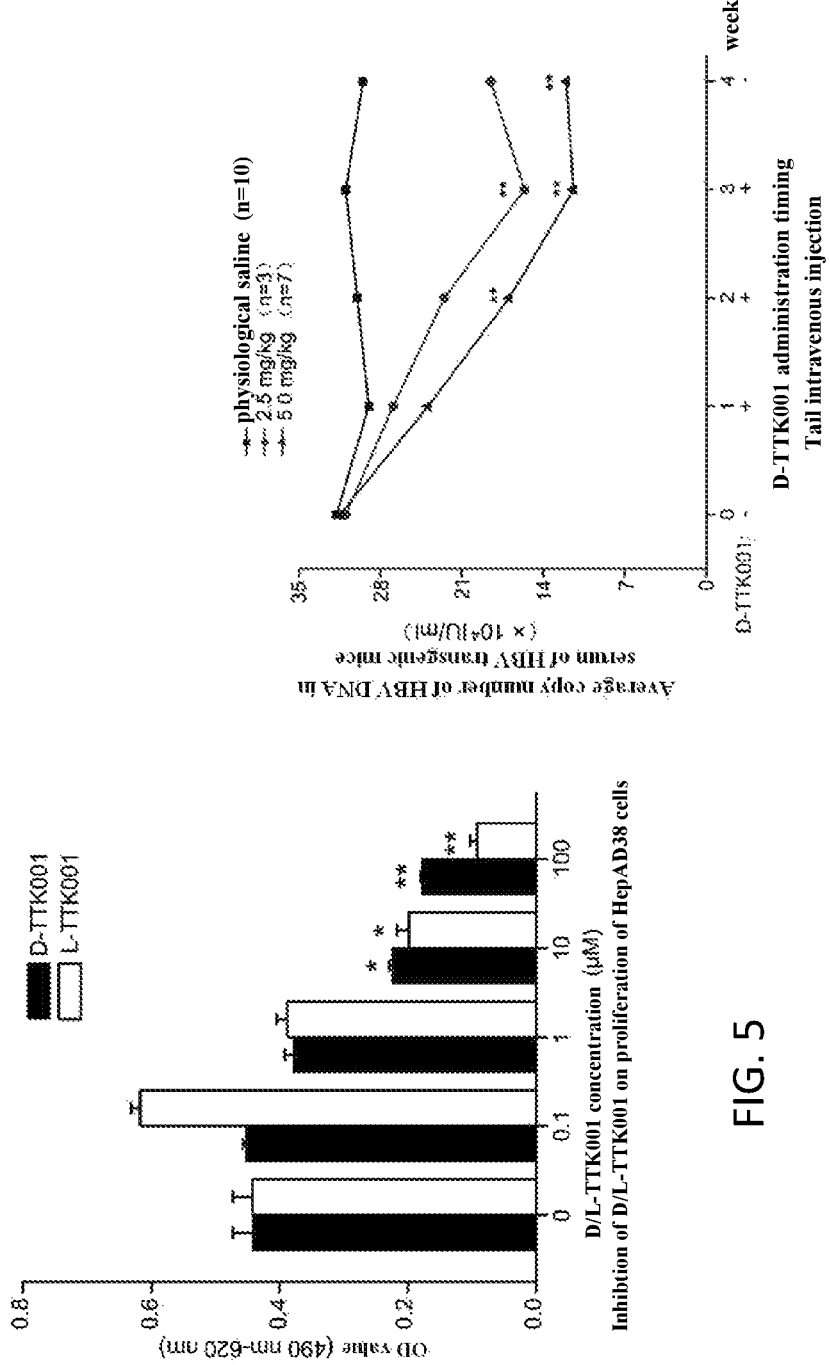
FIG. 5. Analysis of the effects of polypeptides of the invention on proliferation of liver cancer cells HepAD38 integrated with HVB DNA at cellular level by MTT assay. Results showed that proliferation of liver cancer cells HepAD38 integrated with HVB DNA were inhibited after 48 hours treatment with 0.1, 1, 10, and 100 μM of artificially synthesized polypeptide D-TTK001 or L-TTK001 (i.e., anti-HBxP1#) with a dose dependency. Student's t-test is employed for statistical analysis, * $P<0.05$, ** $P<0.01$.
FIG. 6. Analysis of the effects of polypeptide D-TKK001 of the invention on HBV transgenic mice. HBV transgenic mice were treated with artificially synthesized polypeptide D-TKK001 in two groups with doses of 2.5 mg/kg and 5.0 mg/kg respectively by tail intravenous injection; negative control group were treated with PBS by tail intravenous injection. Afterward, copy number of HBV DNA in serum of HBV transgenic mice were measured with real-time PCR. Results showed that copy number of HBV DNA in serum of HBV transgenic mice are clearly reduced by D-TTK001 with a time and dose dependency, suggesting that D-TTK001 has the function of inhibiting HBV DNA replication. Student's t-test is employed for statistical analysis, * $P<0.05$, ** $P<0.01$.

As shown in FIG. 5, D-TTK001 (or L-TTK001) exhibited clear inhibition effect on the growth and proliferation of HepAD38 cells with a dose dependency. Minimum effective dose of D-TTK001 and L-TTK001 are both 10 µM. Student's t-test is employed for statistical analysis, * $P<0.05$, ** $P<0.01$.

Example 3: In Vivo Polypeptide Efficacy Experiments

1. Effect of D-TTK001 on HBV DNA in HBV Transgenic Mice (1) Origin and Characteristics of HBV Transgenic Mice (Guangzhou Junketaite Pharmaceutical Technology Co., Ltd.)

HBV transgenic mice were purchased from Guangzhou Junketaite Pharmaceutical Technology Co., Ltd. The animal model is a 1.3 copies high expressing replicative form HBV whole-genome transgenic mice Tg (HBV 1.3 genome) Swb established using microinjection method by Guangzhou Junketaite Pharmaceutical Technology Co., Ltd. Serum HBsAg and HBeAg can be analyzed with common ELISA kit; serum HBV DNA of 93.93% positive transgenic mice is $10^4\sim10^6$ copy/mL; liver tissues in immunohistochemistry have HBsAg (cytoplasmic type) and HBcAg (karyotype) expression. Neither of gender, month age, or time in a day has a significantly effect, which means stable expression; high serum HBV DNA positive rate can be maintained for a long period (tested in transgenic mice until 39 months old), gender shows no significant effect. This makes a good foundation for the transgenic model to be used in evaluating anti-HBV drugs.

(2) Tail Intravenous Administration (D-TTK001) Method and Blood Sampling Method in HBV Transgenic Mice Prepare D-TTK001 aseptically. Administer 2.5 mg/kg (10 mice) or 5.0 mg/kg (42 mice) based on mice weight through tail intravenous injection in a volume of 50 µL. Administer 50 µL of sterile PBS to blank control group (10 mice). Mice are 6-8 months old, half male and half female. Inject daily for 3 weeks (21 days in total). Take artery blood from mice tail before administration for future measurement of HBV DNA content in mice blood, record as T0 group. Take artery blood from mice tail after one week (T1+ group), two weeks (T2+ group), and three weeks (T3+ group) of administration. Take blood after one week of stopping administration (T4 group). Blood samples were standed in room temperature for 2-4 hours to prepare serum. Store samples in −80° C. refrigerator for future measurement of HBV DNA content in mice blood.

(3) Measurement of Copy Number of HBV DNA with Real-Time PCR Assay (i) Preparation of test samples: Take out the test samples from −80° C. refrigerator. Place it at room temperature for balancing. Take corresponding amount of reaction liquid, enzyme mix and internal standard by proportion (reaction liquid 38 µL per serving+enzyme mix 2 µL per serving+internal standard 0.2 µL per serving) according to numbers of test sample, negative control sample and reference sample, mix sufficiently as PCR-mix. Sample treatment (negative control, positive control quantitative reference and test samples are treated synchronously): Add 5 µL of cell nucleic releaser into each PCR reaction tube, then add 5 μL test sample into each tube, absorb back and forth for 3-5 times and mix; after more than 10 minutes interval, add 40 μL of PCR-mix into each tube, close the tubes with caps, centrifuge at 2000 rpm for 30 seconds.

(ii) PCR Amplification

Utilizing real time PCR HBV DNA assay kit manufactured by Sun Yat-sen University Daan Gene Co., Ltd. according to the manufacturer's specification as followed: Place PCR reaction tube into sample cell of PCR instrument, set negative control, positive control, quantitative references A-D and test sample in corresponding order, and then set sample name and concentration of quantitative reference. Selection of fluorescence detection channel: for example, in ABI 7300 instrument, i) select FAM channel (reporter: FAM, quencher: none) to detect HBV-DNA; ii) select HEX/VIC channel (reporter: HEX/VIC, quencher: none) to detect HBV-internal standard; iii) set passive reference as ROX.

Cycle Parameters were Set as Followed:

| UNG enzyme reaction | 50° C. | 2 min | 1 cycle |
| Taq enzyme activation | 94° C. | 5 min | 1 cycle |
| Degradation | 94° C. | 15 sec | 45 cycle |
| Quenching, extension, and fluorescent intensity | 57° C. | 30 sec | 1 cycle |
| Instrument cooling | 25° C. | 10 sec | 1 cycle |

(iii) Result Analysis:

Set analysis conditions: adjust start value, stop vale of Baseline and Value of Threshold according to analyzed image (arbitrary adjustable by user according to actual needs, start value can be 1~10, stop value can be 5~10, Value can be 0.01~0.2) to optimize standard curve in "Std curve" window, i.e., correlation between −1.0~−0.97. Select "Analyze" in "Analysis" menu for automatic result analysis. Record value (C) of unknown variable in "Tray" window. "C" indicates concentration or content of the sample.

(iv) Quality Control:

Negative QC sample: no Ct value; but HBV-inner wall inspection is positive (Ct value≤40).

Positive QC sample: measured concentration between $1.26 \times 10^5 \sim 1.26 \times 10^6$ IU/mL.

Four positive quantitative references: all positive with a linear correlation coefficient of $0.98 \leq |r| \leq 1$.

All above requirements must be satisfied in one experiment, otherwise the experiment is invalid and need to be re-performed.

Copy number of HBV DNA in serum of HBV transgenic mice were measured with real-time PCR. Results of 2.5 mg/kg group: effective rate is 30% (3 out of 10 mice) from one week (T1+ group) with a clear time dependency. In 5.0 mg/kg group, effective rate is 54.8% (23 out of 42 mice). Effective rate is 46.2% (18 out of 39 mice) from one week (T1+ group), wherein a time dependent decreasing effective rate is 30.4% (7 out of 23 mice). As shown in FIG. 6, suggested by a comparison of the time dependent decreasing efficacies between 3 mice of 2.5 mg/kg group and 7 mice from 5.0 mg/kg group, pharmacological function of inhibition of D-TTK001 on HBV replication at HBV transgenic animal level was dose dependent.

2. Pathological Observation of Liver Tissue of HBV Transgenic Mice after D-TTK001 Treatment After above experiments on HBV transgenic mice were finished, mice were sacrificed, and liver tissue was taken, fixed with formalin, embed with conventional method, to prepare tissue biopsies, pathological observation was then conducted.

Figure 7:
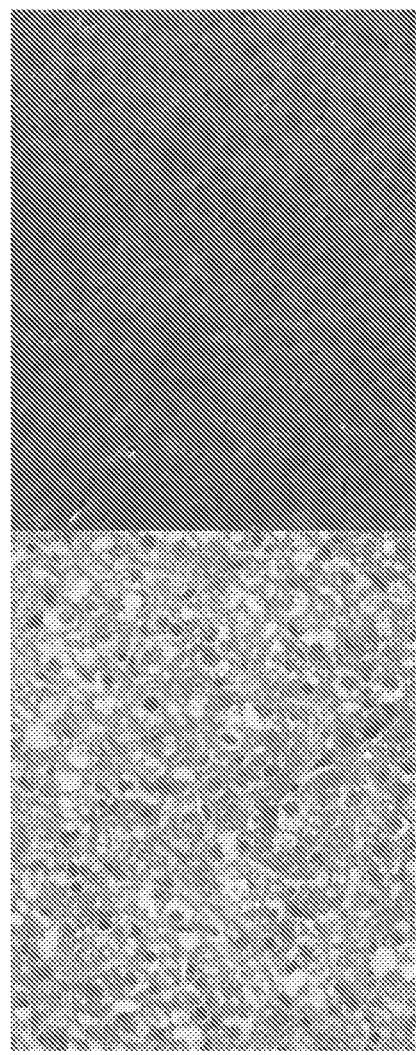
FIG. 7. Analysis of treatment effects of artificially synthesized polypeptide D-TKK001 on hepatitis in HBV transgenic mice. Left panel shows liver pathologic tissue of HBV transgenic mice; 6 out of 10 HBV transgenic mice in untreated control group showed typical pathological features of viral hepatitis such as ballooning degeneration of hepatocytes. Right panel shows liver tissue after 3 weeks treatment with D-TTK001 (5 mg/kg) by tail intravenous injection; none of 6 mice in experimental group showed ballooning degeneration of hepatocytes, suggesting that D-TTK001 has a clear treatment effect on pathological hepatitis lesions in liver tissue.

Treatment effects of artificially synthesized polypeptide D-TKK001 on hepatitis in HBV transgenic mice are shown in FIG. 7. Left panel shows liver pathologic tissue of HBV transgenic mice; 6 out of 10 HBV transgenic mice in untreated control group showed typical pathological features of viral hepatitis such as ballooning degeneration of hepatocytes. Right panel shows liver tissue after 3 weeks treatment with D-TTK001 (5 mg/kg) by tail intravenous injection; none of 6 mice in experimental group showed ballooning degeneration of hepatocytes, suggesting that D-TTK001 has a clear treatment effect on pathological hepatitis lesions in liver tissue.

3. Effect of D-TTK001 on Inoculated Tumor Bearing Nude Mice

Suspend HepG2-X cells at exponential phase by treating with trypsin, count the number of cells, dilute to $1 \times 10^7$ cells/mL with sterile physiological saline, and then store in ice water. Take two female BALB/C mice of 4~6 weeks age: i) one mouse in control group, inject 0.2 mL of above diluted cells to the armpit of right forelimb for each mouse, then only inject 0.5 mL of sterilized distilled water (without polypeptide drugs); ii) one mouse in experimental group with an administration dose of 10 mg/kg weight. Inject 0.2 mL of above diluted cells to the armpit of right forelimb for each mouse, after 20 days of injection, remove tumor tissue aseptically, cut into small tissue pieces, back inoculate to female BALB/C mice of 4~6 weeks age for 18 mice in total. After tumor volume ($V=L \times W^2$ 0.5) reaches 100 mm$^3$, divide 18 mice into 3 groups each having 6 mice. The first group is control group, tail intravenous injecting with sterile PBS. The second group is experimental group, tail intravenous injecting with 0.1 mg/kg D-TTK001. The third group is experimental group, tail intravenous injecting with 0.5 mg/kg D-TTK001 (lyophilized polypeptide dissolved in 0.5 mL sterilized distilled water). Inject daily for 30 days, measure mice weight and tumor volume before each injection, and observe survival time of nude mice. After mice dies, perform analysis using Kaplan-Meier method to plot survival curve, Log-Rank is employed for statistical analysis.

Figure 8:
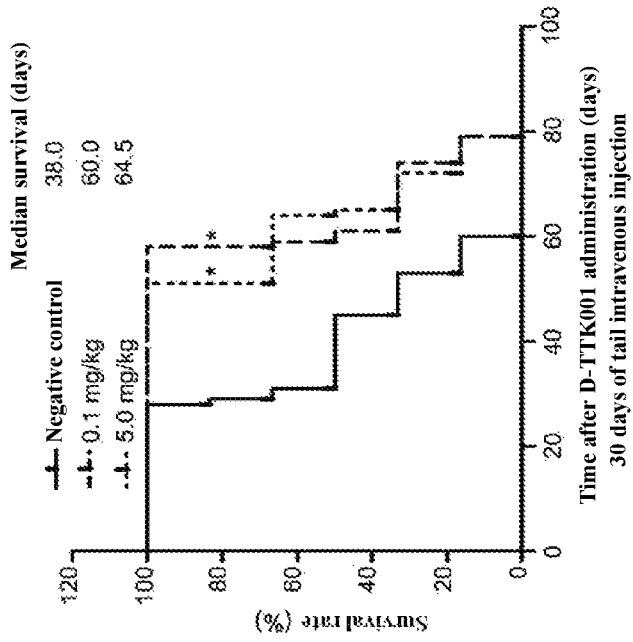
FIG. 8. Analysis of effects of artificially synthesized polypeptide D-TKK001 on survival rate of liver cancer bearing nude mice. Results of animal experiments showed that survival rates of tumor bearing nude mice inoculated with HepG2-X cells were clearly prolonged in groups treated with artificially synthesized D-TTK001 polypeptide at 0.1 mg/kg or 5.0 mg/kg, suggesting that D-TTK001 has a function of inhibiting malignant phenotype of HepG2-X cells inoculated tumor in nude mice. Log-Rank is employed for statistical analysis, * $P<0.5$.

As shown in FIG. 8, experimental results showed that survival time of tumor bearing nude mice inoculated with HepG2-X cells were clearly prolonged in groups treated with artificially synthesized D-TTK001 polypeptide at 0.1 mg/kg or 5.0 mg/kg, suggesting that D-TTK001 has a function of inhibiting malignant phenotype of HepG2-X cells inoculated tumor in nude mice. Log-Rank is employed for statistical analysis, * P<0.5.

Example 4: Functional Fragments and Functional Variants of Polypeptide

The invention also investigates the role of the functional variants of the polypeptide and functional fragments thereof. The sequences as shown in the following table are artificially synthesized D-amino acid substituted sequences on the basis of L-TTK001 (i.e., anti-HBxP1#). The polypeptide fragments were artificially synthesized according to the sequences (method as above), and then, above-mentioned ELISA method was adopted to observe the change in the functions of the polypeptides.

TABLE 2B

| Synthesized polypeptide fragments | Amino acid sequences | SEQ ID NO. |
|---|---|---|
| D-TTK001 | Gly-D-Ser-D-Ala-D-Val-D-Met-D-Phe-D-Ser-D-Ser-D-Lys-D-Glu-D-Arg-Gly<br>or G-D/S-D/A-D/V-D/M-D/F-D/S-D/S-D/K-D/E-D/R-G | 1 |
| D-TTK001-1 | Gly-D-Ser-Ala-Val-Met-Phe-Ser-Ser-Lys-Glu-Arg-Gly<br>or G-D/S-A-V-M-F-S-S-K-E-R-G | 2 |
| D-TTK001-2 | Gly-D-Ser-Ala-Val-Met-Phe-Ser-Ser-Lys-Glu-Arg-Gly<br>or G-S-D/A-V-M-F-S-S-K-E-R-G | 3 |
| D-TTK001-3 | Gly-D-Ser-Ala-Val-Met-Phe-Ser-Ser-Lys-Glu-Arg-Gly<br>or G-S-A-D/V-M-F-S-S-K-E-R-G | 4 |
| D-TTK001-4 | Gly-D-Ser-Ala-Val-Met-Phe-Ser-Ser-Lys-Glu-Arg-Gly<br>or G-S-A-V-D/M-F-S-S-K-E-R-G | 5 |
| D-TTK001-5 | Gly-D-Ser-Ala-Val-Met-Phe-Ser-Ser-Lys-Glu-Arg-Gly<br>or G-S-A-V-M-D/F-S-S-K-E-R-G | 6 |
| D-TTK001-6 | Gly-D-Ser-Ala-Val-Met-Phe-Ser-Ser-Lys-Glu-Arg-Gly<br>or G-S-A-V-M-F-D/S-S-K-E-R-G | 7 |
| D-TTK001-7 | Gly-D-Ser-Ala-Val-Met-Phe-Ser-Ser-Lys-Glu-Arg-Gly<br>r G-S-A-V-M-F-S-D/S-K-E-R-G | 8 |
| D-TTK001-8 | Gly-D-Ser-Ala-Val-Met-Phe-Ser-Ser-Lys-Glu-Arg-Gly<br>or G-S-A-V-M-F-S-S-D/K-E-R-G | 9 |
| D-TTK001-9 | Gly-D-Ser-Ala-Val-Met-Phe-Ser-Ser-Lys-Glu-Arg-Gly<br>or G-S-A-V-M-F-S-S-K-D/E-R-G | 10 |
| D-TTK001-10 | Gly-D-Ser-Ala-Val-Met-Phe-Ser-Ser-Lys-Glu-Arg-Gly<br>or G-S-A-V-M-F-S-S-K-E-D/R-G | 11 |

Figure 9:
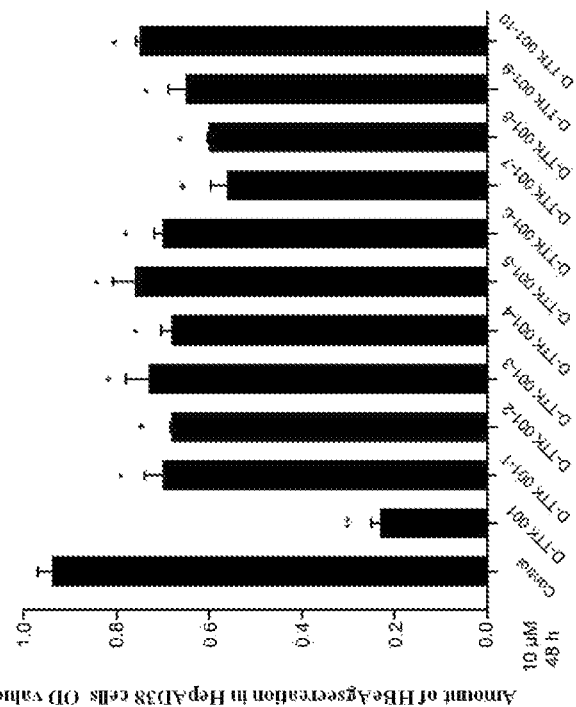
FIG. 9. Analysis of the effects of polypeptides of the invention on HBeAg secretion levels of liver cancer cells HepAD38 integrated with HVB DNA at cellular level. Results showed that HBeAg secretion levels of liver cancer cells HepAD38 integrated with HVB DNA were inhibited after 48 hours treatment with 10 μM of each of artificially synthesized polypeptide D-TTK001 or polypeptide as shown in SEQ ID NOs: 2-11 (e.g., D-TTK001-1, D-TTK001-2, D-TTK001-3, D-TTK001-4, D-TTK001-5, D-TTK001-6, D-TTK001-7, D-TTK001-8, D-TTK001-9, D-TTK001-10) with a dose dependency. Student's t-test is employed for statistical analysis, * $P<0.05$, ** $P<0.01$.

As shown in FIG. 9, 10 μM of each of D-TTK001-1, D-TTK001-2, D-TTK001-3, D-TTK001-4, D-TTK001-5, D-TTK001-6, D-TTK001-7, D-TTK001-8, D-TTK001-8, D-TTK001-9, D-TTK001-10 inhibits HBeAg secretion levels of HepAD38 cells to various extents, wherein D-TTK001 has the most significant effect, suggesting that individual substitutions with artificially synthesized D-amino acid change conformation of L-TTK001 (i.e., anti-HBxP1#) polypeptide, thus affecting biological activities thereof to various extents. In addition, stability of polypeptide is enhanced with increasing number of D-amino acid substitutions. While biological activities of D-TTK001 and L-TTK001 are similar to each other, suggesting the symmetric isomer maintains the binding ability to target HBx protein. Student's t-test is employed for statistical analysis, * $P<0.05$, ** $P<0.01$.

Example 5: In Vivo Pharmacokinetic Experiments of Polypeptide Drugs in Rats 6 experiment animals were intravenous injected with 3.6 mg/kg D-TTK001 solution (equivalent to 5 mg/kg in mice). Blood samples were collected and placed the heparinized test tubes according to blood collection times. Plasma concentration of D-TTK001 in rats was measured by Triple-TOF mass spectrometer.

Major pharmacokinetic parameters after intravenous injection of 3.5 mg/kg D-TTK001 in 6 rats were shown in Table 3, wherein a half-life was 55.27 min.

TABLE 3

Major pharmacokinetic parameters after intravenous injection of 3.5 mg/kg D-TTK001 in 6 rats

| Pharmacokinetic parameters | 01 | 02 | 03 | 04 | 05 | 06 | Mean | SD |
|---|---|---|---|---|---|---|---|---|
| $C_{max}$ (μg/mL) | 75.70 | 32.90 | 31.60 | 26.90 | 28.40 | 19.60 | 35.85 | 20.07 |
| $C_0$ (μg/mL) | 80.53 | 27.93 | 31.15 | 28.97 | 31.91 | 18.27 | 36.46 | 22.14 |
| $t\frac{1}{2}$ (min) | 31.28 | 58.07 | 99.44 | 41.40 | 56.30 | 45.09 | 55.27 | 23.80 |
| AUC0-t (μg/mL * min) | 1165.52 | 1073.22 | 2299.13 | 742.46 | 1221.15 | 998.81 | 1250.05 | 540.48 |
| AUC0-∞ (μg/mL * min) | 1180.24 | 1177.75 | 3151.72 | 770.73 | 1361.37 | 1051.30 | 1448.85 | 856.85 |
| V (L/kg) | 0.134 | 0.249 | 0.159 | 0.271 | 0.209 | 0.217 | 0.207 | 0.052 |
| CL (L/min/kg) | 0.003 | 0.003 | 0.001 | 0.005 | 0.003 | 0.003 | 0.003 | 0.001 |

Example 6: Polypeptide Drugs Acute Toxicity Test

Control group and experimental group each consists of 10 Kunming white mice, with 5 females and 5 males in each group, respectively. Experimental group were injected with polypeptide D-TTK001 with the concentration of 500 mg/kg (10 mg lyophilized polypeptide dissolved in 0.8 mL sterilized distilled water) by tail intravenous injection; control group were injected with 0.8 mL sterilized distilled water. Consecutively observing the mice for 24 hrs. after injection.

The polypeptide drug acute toxicity test showed that the mice do not have abnormal behaviors, and no abnormal changes in weight as compared with control group.

All references, including publications, patent applications, and patents, cited herein are hereby incorporated and were set forth in its entirety herein. The use of any and all examples, or exemplary language (e.g., "such as") provided herein, is intended merely to better illustrate the invention and does not pose a limitation on the scope of the invention unless otherwise specified. Preferred embodiments of this invention are described herein, including the best mode known to the inventors for carrying out the invention. Variations of those preferred embodiments may become apparent to those of ordinary skill in the art upon reading the foregoing description. The inventors expect those skilled in the art to employ such variations as appropriate, and the inventors intend for the invention to be practiced otherwisely than as specifically described herein. The invention includes all modifications and equivalents of the subject matter recited in the claims appended hereto as permitted by applicable law unless otherwise indicated herein or otherwise clearly contradicted by context.

The invention claimed is:

1. An isolated polypeptide, comprising the amino acid sequence as shown in SEQ ID NO:1 or a functional variant having at least 70% identity with SEQ ID NO:1, wherein said polypeptide is capable of inhibiting hepatitis B virus X protein, and capable of inhibiting the occurrence and development of chronic liver diseases resulting from hepatitis B virus infection.

2. The polypeptide according to claim 1, wherein the amino acid sequence of the polypeptide consists of the amino acid sequence as shown in SEQ ID NO: 1.

3. The polypeptide according to claim 1, wherein said chronic liver diseases resulting from hepatitis B virus infection are selected from the group consisting of hepatitis, hepatic cirrhosis, and liver cancer.

4. A pharmaceutical composition comprising the polypeptide according to claim 1 and a pharmaceutical carrier.

5. A pharmaceutical composition comprising the polypeptide according to claim 2 and a pharmaceutical carrier.

6. A method of treating a chronic liver disease resulting from hepatitis B virus infection, comprising administering to one in need thereof the pharmaceutical composition of claim 4.

7. A method of treating a chronic liver disease resulting from hepatitis B virus infection, comprising administering to one in need thereof the pharmaceutical composition of claim 5.

8. The method according to any one of claims 6-7, wherein said chronic liver diseases are selected from the group consisting of hepatitis, hepatic cirrhosis, and liver cancer.

* * * * *